(12) United States Patent
Seaver et al.

(10) Patent No.: US 9,381,331 B2
(45) Date of Patent: Jul. 5, 2016

(54) DEVICE FOR REGULATING GRAVITATIONAL PRESSURE IN A SHUNT SYSTEM

(71) Applicant: Arkis Biosciences, Knoxville, TN (US)

(72) Inventors: Chad Seaver, Knoxville, TN (US); Chris Arnott, Knoxville, TN (US); James Alexander Killeffer, Knoxville, TN (US)

(73) Assignee: Arkis Biosciences, Knoxville, TN (US)

( * ) Notice: Subject to any disclaimer, the term of this patent is extended or adjusted under 35 U.S.C. 154(b) by 374 days.

(21) Appl. No.: 13/948,639

(22) Filed: Jul. 23, 2013

(65) Prior Publication Data

US 2014/0024995 A1    Jan. 23, 2014

Related U.S. Application Data (60) Provisional application No. 61/674,729, filed on Jul. 23, 2012.

(51) Int. Cl.
| | | |
|---|---|---|
| *A61M 27/00* | (2006.01) | |
| *A61M 39/22* | (2006.01) | |
| *A61M 39/24* | (2006.01) | |

(52) U.S. Cl.
CPC ........... *A61M 27/006* (2013.01); *A61M 39/227* (2013.01); *A61M 39/24* (2013.01); *A61M 2039/242* (2013.01); *A61M 2039/248* (2013.01); *A61M 2210/0693* (2013.01); *A61M 2230/62* (2013.01)

(58) Field of Classification Search
CPC . A61M 27/006; A61M 39/227; A61M 39/24; A61M 2210/0693; A61M 2039/242; A61M 2039/248
See application file for complete search history.

(56) References Cited

U.S. PATENT DOCUMENTS

| | | |
|---|---|---|
| 3,889,687 A | 6/1975 | Harris et al. |
| 4,731,056 A | 3/1988 | Tremulis |
| 5,368,556 A | 11/1994 | Lecuyer |
| 5,527,295 A | 6/1996 | Wing |

(Continued)

FOREIGN PATENT DOCUMENTS

| | | |
|---|---|---|
| EP | 19840400017 | 9/1988 |
| EP | 1587557 | 11/2006 |
| EP | 1613388 | 2/2008 |

OTHER PUBLICATIONS

Integra NeuroSciences; Gravity Compensating Accesory; Integra NeuroSciences Implants S.A., 2002.

(Continued)

*Primary Examiner* — Philip R Wiest
*Assistant Examiner* — Benjamin Klein
(74) *Attorney, Agent, or Firm* — Pitts & Lake. P.C.

(57) ABSTRACT

A gravitational pressure regulating valve to regulate fluid flow of a patient, including a fluid chamber having an inlet port to receive a bodily fluid and an outlet port to discharge the received bodily fluid, and an opposing force member in the fluid chamber to oppose a first force of the fluid flow at the inlet port with a second force that varies according to changes in gravitational alignment.

9 Claims, 6 Drawing Sheets

(56) References Cited

U.S. PATENT DOCUMENTS

| | | |
|---|---|---|
| 5,634,894 A | 6/1997 | Magarm |
| 6,383,160 B1 | 5/2002 | Madsen |
| 6,953,444 B2 | 10/2005 | Rosenberg |
| 7,282,040 B2 | 10/2007 | Hokanson |
| 8,088,092 B2 | 1/2012 | McCusker et al. |
| 2002/0026139 A1 | 2/2002 | Bertrand |
| 2005/0038371 A1* | 2/2005 | Reich et al. .................. 604/9 |
| 2006/0089589 A1 | 4/2006 | Portnoy |

OTHER PUBLICATIONS

Gravity Assited Valve; Patientenhandbuch; Christopher Miethke GMBH & CO.KG; http://miethke.com/pdf/GAV_PH.pdf.

Gravity Assisted Valve; Gebrauchsanweisung; Christopher Miethke GMBH & CO. KG; http://miethke.com/pdf/GAV_GBA.pdf.

PCT; International Search Report (PCT Article 18 and Rules 43 and 44); Date of Mailing: Nov. 22, 2013; International Searching Authority.

* cited by examiner

DEVICE FOR REGULATING GRAVITATIONAL PRESSURE IN A SHUNT SYSTEM

CROSS-REFERENCE TO RELATED APPLICATIONS

This application claims priority from U.S. Provisional Application No. 61/674,729, filed on Jul. 23, 2012.

FIELD OF INVENTION

The present general inventive concept relates generally to a pressure regulating valve in a shunt system, and, more particularly, to a pressure regulating valve to compensate for the force of gravity on bodily fluid in a shunt system that occurs when a patient is upright.

BACKGROUND

The human cranial vault contains the brain, blood vessels, and cerebrospinal fluid (CSF). The sutures of the cranium fuse by a year of age and the skull becomes a rigid structure. The architecture and physiology of the intracranial space allow for some compensation for additional intracranial volume such as hemorrhage, tumor, or excess CSF. When this compensatory capacity is exhausted, the contents act essentially as ideal fluids in a rigid container, making them subject to rapid rises in pressure when a relatively small volume of fluid is added. With sufficient rise in intracranial pressure (ICP), brain tissue is compressed and its blood supply is compromised resulting in brain damage and, if unchecked, death.

In the normal brain, CSF is secreted by tissue known as choroid plexus within cavities in the brain called ventricles. The CSF flows from the uppermost lateral ventricles through conduits into the more central third and then fourth ventricles, then flowing out of the brain to surround the spinal cord and brain. Ultimately, the CSF is absorbed on the outer surface of the brain by cells comprising the arachnoid villi. This is a continuous circulation, amounting to approximately 400 cc/day. Any interruption in CSF circulation can result in excess CSF within the intracranial space, a condition known as hydrocephalus. In mild cases, CSF fills the ventricles excessively and stretches the cells of the brain resulting in neurological dysfunction. In severe cases, the rise in ICP may be sufficient to result in brain damage or death.

The most common contemporary treatment of hydrocephalus is to divert the flow of CSF. CSF is diverted to a space in the body that has a large capacity to absorb it such as the peritoneum, pleura, or bloodstream. A shunt for CSF diversion typically consists of a synthetic tube placed through a hole drilled in the skull and passed through the brain and terminates in the desired drainage location. Lumboperitoneal shunting is also possible, which avoids the need to drill into the skull by instead draining CSF from the lumbar region of spinal column, but is at greater risk of siphoning. The shunt may be fitted with a valve designed to control pressure and flow as well as a device designed to retard over-drainage due to siphoning with upright posture.

Currently available shunt technology has several shortcomings. Valve technology is often inadequate to provide the optimal level of drainage. Under-drainage results in elevated ICP and over-drainage can result in headaches or hemorrhage due to collapse of the brain and tearing of surface blood vessels. Differential pressure based shunts, even with "anti-siphon countermeasures," often do not adapt well to changes in posture, to fluctuating CSF production and ICP, or to changes in intracranial CSF dynamics over time. Patients with shunts and persistent headaches frequently present a challenge because it is unclear whether there is subtle over- or under-drainage. The simple externally adjustable valves available currently force the clinician to guess at the appropriate pressure setting and accept that the system cannot adapt to fluctuations in demand.

CSF siphoning occurs when patient position creates additional pressure in the shunt due to gravitational forces on the fluid column within the shunt and its tubing. This excess pressure is exerted across the shunt's differential valve, causing it to activate and undesirably allow CSF fluid to flow. This unwanted parasitic flow can reduce patient quality of life and can lead to numerous serious life threatening conditions by excess removal of CSF from the patient's brain. A significant source of this unwanted siphoning is the error pressure, as viewed from the valve, generated by the force produced by the weight of the CSF fluid contained within the shunt tubing between the proximal catheter and the shunt tubing, and the distal catheter exit.

In the case of lumboperitoneal shunting, the CSF contained within the spinal column is the source of the error pressure generation. The pressure generated by the weight of the CSF in the spinal column can easily exceed the set point of differential valves in the shunt and lead to siphoning. A patient's motion and position affects how much error pressure is generated; minimum siphoning occurs when the patient and the shunt's flow path are supine, and maximum siphoning occurs when upright. This parasitic siphoning is a reason why the less costly and less complex surgical procedure of lumboperitoneal shunt treatment is not a more prevalent treatment option for hydrocephalus. Thus, there exists a desire for an anti-siphon device that prevents over drainage of CSF fluid regardless of patient position or activity.

BRIEF SUMMARY

The present general inventive concept provides a gravitational pressure regulating valve to regulate fluid flow of a patient, including a fluid chamber having an inlet port to receive a bodily fluid and an outlet port to discharge the received bodily fluid, and an opposing force member in the fluid chamber to oppose a first force of the fluid flow at the inlet port with a second force that varies according to changes in gravitational alignment.

Additional aspects and advantages of the present general inventive concept will be set forth in part in the description which follows, and, in part, will be obvious from the description, or may be learned by practice of the present general inventive concept.

The foregoing and/or other aspects and advantages of the present general inventive concept may be achieved by a gravitational pressure regulating valve to regulate fluid flow of a patient, including a fluid chamber having an inlet port to receive a bodily fluid and an outlet port to discharge the received bodily fluid, and a buoyant member provided in the fluid chamber and configured to oppose a first force of the fluid flow at the inlet port with a second force that varies according to changes in gravitational field alignment in the fluid chamber due to the orientation of the valve.

The buoyant member may be configured to close the inlet port in response to the second force exceeding the first force.

The buoyant member may be substantially spherical.

The gravitational pressure regulating valve may further include a permeable guide member provided in the fluid chamber and configured to allow bidirectional movement of the buoyant member within the guide member.

The gravitational pressure regulating valve may further include a biasing member coupled to the buoyant member and the guide member to augment the second force.

The gravitational pressure regulating valve may further include one or more additional buoyant members to augment the second force.

The gravitational pressure regulating valve may further include a guide member coupled to the fluid chamber and the buoyant member to guide the buoyant member to and from the inlet port in a substantially reciprocating path.

The second force may have a maximum value in response to the inlet port being directly above the one or more buoyant members.

The buoyant member may remain substantially seated in and centrally aligned with the inlet port regardless of the orientation of the valve.

The foregoing and/or other aspects and advantages of the present general inventive concept may also be achieved by a gravitational pressure regulating valve to regulate fluid flow of a patient, including a fluid chamber having an inlet port to receive a bodily fluid and an outlet port to discharge the received bodily fluid, and a plurality of weighted members provided in the fluid chamber and configured to oppose a first force of the fluid flow at the inlet port with a second force that varies according to changes in gravitational alignment of the weighted members due to the orientation of the valve, wherein at least a portion of an inner surface of the fluid chamber is configured to be substantially conical around the inlet port such that a first one of the weighted members closest to the inlet port is offset from any remaining weighted members in the direction of the inlet port.

The first one of the weighted members may be configured to close the inlet port in response to the second force exceeding the first force.

The weighted members may be substantially spherical.

The second force may have a maximum value in response to the inlet port being directly below the first one of the weighted members.

The fluid chamber may be configured to limit movement of the weighted members such that the first one of the weighted members will remain closest to the inlet port regardless of the orientation of the valve.

The fluid chamber may be configured to limit movement of the weighted members such that the first one of the weighted members will always be in contact with at least one remaining weighted member.

The second force may be a combination of vector forces from each of the weighted members in response to the inlet port being directly below the first one of the weighted members.

The weighted members may each be configured to have a greater density than the bodily fluid moving in and out of the fluid chamber.

The foregoing and/or other aspects and advantages of the present general inventive concept may also be achieved by a gravitational pressure regulating valve to regulate fluid flow of a patient, including a fluid chamber having an inlet port to receive a bodily fluid and an outlet port to discharge the received bodily fluid, a variable resistance flow valve provided in the fluid chamber and configured to oppose a first force of the fluid flow at the inlet port with a second force applied to the variable resistance flow valve, an opposing force member configured to apply the second force to the variable resistance flow valve, and a reference unit sensitive to gravitational alignment changes to cause the opposing force member to vary the second force according to the gravitational alignment changes.

The opposing force member may be a diaphragm coupled to the variable resistance flow valve.

The reference unit may include a reference fluid column in direct communication with the diaphragm, the diaphragm may separate the bodily fluid and fluid from the reference fluid column, and the reference fluid column may be configured such that changes in the gravitational alignment of the reference fluid column correspond to changes in the gravitational pressure at the inlet port.

The gravitational pressure regulating valve may further include a predetermined amount of gas forming an interface with the reference fluid column to allow compression in the diaphragm resulting from an opening of the variable resistance flow valve.

The gravitational pressure regulating valve may further include a housing to house the reference fluid column and gas, and an air bleeder port to remove air from the housing when the housing is being filled with liquid.

The reference unit may include a gravitational alignment sensor, and may be in electrical communication with the opposing force member to cause the opposing force member to vary the second force according to the gravitational alignment changes.

Other features and aspects may be apparent from the following detailed description, the drawings, and the claims.

BRIEF DESCRIPTION OF THE FIGURES

The following example embodiments are representative of example techniques and structures designed to carry out the objects of the present general inventive concept, but the present general inventive concept is not limited to these example embodiments. In the accompanying drawings and illustrations, the sizes and relative sizes, shapes, and qualities of lines, entities, and regions may be exaggerated for clarity. A wide variety of additional embodiments will be more readily understood and appreciated through the following detailed description of the example embodiments, with reference to the accompanying drawings in which.

DETAILED DESCRIPTION

Reference will now be made to various example embodiments of the present general inventive concept, examples of which are illustrated in the accompanying drawings and illustrations. The example embodiments are described herein in order to explain the present general inventive concept by referring to the figures.

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. The described progression of processing operations described are merely examples, however, and the sequence of operations is not limited to that set forth herein and may be changed as is known in the art, with the exception of operations necessarily occurring in a certain order. Also, description of well-known functions and constructions may be omitted for increased clarity and conciseness.

Note that spatially relative terms, such as "up," "down," "right," "left," "beneath," "below," "lower," "above," "upper" and the like, may be used herein for ease of description to describe one element or feature's relationship to another element(s) or feature(s) as illustrated in the figures. Spatially relative terms are intended to encompass different orientations of the device in use or operation in addition to the orientation depicted in the figures. For example, if the device in the figures is turned over or rotated, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Various example embodiments of the present general inventive concept, as described herein, provide a gravitational pressure regulating valve to regulate fluid flow in a patient, including a fluid chamber having an inlet port to receive a bodily fluid and an outlet port to discharge the received bodily fluid, and an opposing force member in the fluid chamber to oppose a first force of the fluid flow at the inlet port with a second force that varies according to changes in gravitational alignment. Various example embodiments of the present general inventive concept may employ one or more buoyant or weighted elements acting directly on an inlet port to counter a fluid pressure increase caused by increased gravitational pull that occurs when a patient moves from a supine to an upright position. Other various example embodiments of the present general inventive concept may employ a valve that is controlled by other gravity sensitive elements.

Although various example embodiments of the present general inventive concept provide a gravitational pressure regulating valve to regulate fluid flow in a patient, the descriptions herein may generally describe a CSF flow regulating device to prevent siphoning in a hydrocephalus shunt system. However, it is understood that various example embodiments of the present general inventive concept may be used to regulate other types of fluid flow in other types of procedures and/or systems. Also, while fluid flow "in" a patient may be discussed in the descriptions of various example embodiments of the present general inventive concept, it is understood that embodiments of the present general inventive concept may be utilized inside and/or outside of the patient, and therefore the fluid flow being regulated could be occurring inside and/or outside of the patient.

With reference to the following descriptions of the drawings, there is generally illustrated and described an antisiphon device. Various example embodiments of the present general inventive concept can be utilized to realize an antisiphon device that prevents unwanted CSF siphoning in a hydrocephalus shunt treatment. The present general inventive concept alleviates various limitations associated with the conventional hydrocephalus shunt CSF siphoning problems with a novel antisiphon device that aids in preventing CSF siphoning regardless of patient position. The gravitational pressure regulating valve according to various example embodiments of the present general inventive concept may be incorporated into existing hydrocephalus shunt systems already in place in a patient. For example, the gravitational pressure regulating valve may simply be applied at the distal end of an existing shunt system to compensate for the increased force that gravity provides to CSF flow when a patient is upright. In other words, a device according to an embodiment of the present general inventive concept may be retrofitted to an existing system with a relatively simple surgery.

Figure 1:
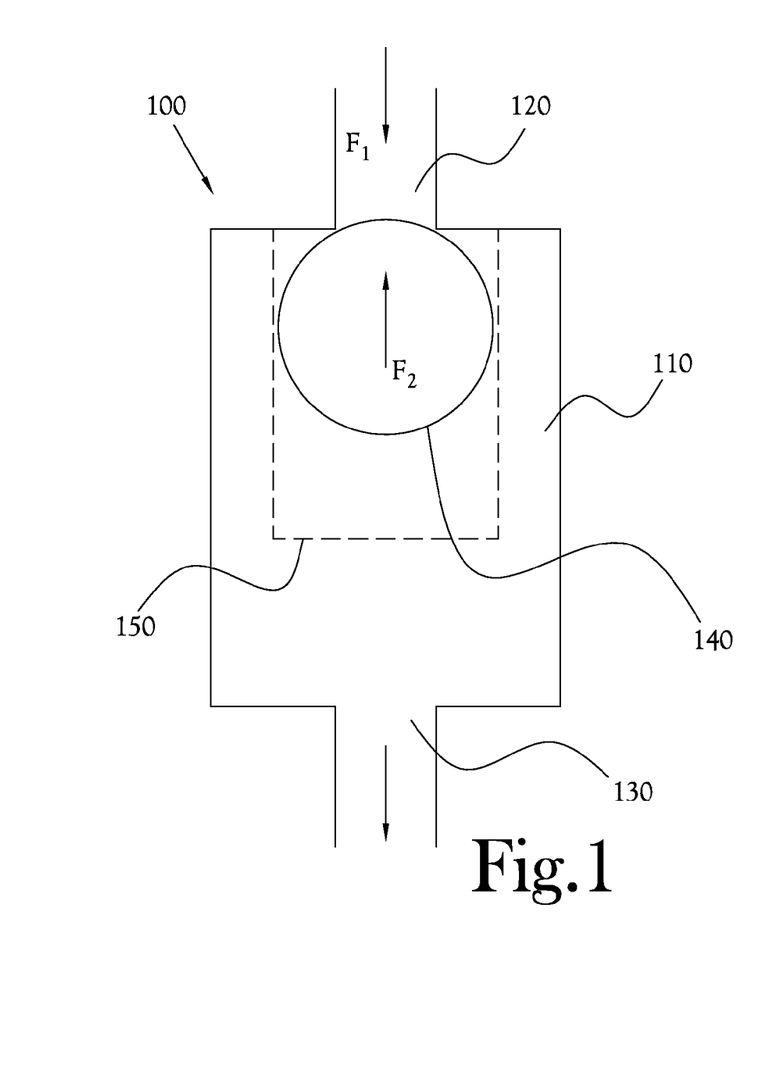
FIG. 1 illustrates a gravitational pressure regulating valve according to an example embodiment of the present general inventive concept.

FIG. 1 illustrates a gravitational pressure regulating valve according to an example embodiment of the present general inventive concept. The gravitational pressure regulating valve 100 of FIG. 1 includes a fluid chamber 110 having an inlet port 120 and an outlet port 130, and a buoyant member 140 provided in the fluid chamber 110. Fluid flows into the inlet port 120 at a first force F1, and the buoyant member 140 opposes the fluid flow with a second force F2. Both of forces F1 and F2 may vary according to changes in the pressure acting on the system caused by changes in gravitational field alignment. In other words, as changes occur in the gravitational field alignment, accumulated weight of the fluid may increase the first force F1, and a component of the buoyant force vector of the buoyant member 140 in the fluid chamber may increase the second force F2. For example, the force F1 of the fluid flow includes the normal drainage force which moves the CSF from the cranium of the patient, but the force F1 is increased when the patient is upright, due to the extra force gravity is placing on the fluid. Therefore, to counter the effects that gravity has on F1, the gravitational alignment of the buoyant member 140 with respect to the inlet port 120 increases the seating force of the buoyant member 140, and therefore the opposing force F2 is increased. In other words, the forces F1 and F2 approach their maximum values when the patient and valve are completely vertical. When the patient is in a horizontal position, the gravitational effect of F1 and F2 approach their minimum values. The changes in these forces caused by gravitational alignment and the weight of the fluid may be generally referred to as changes in gravitational pressure in the descriptions of various example embodiments of the present general inventive concept.

When the opposing second force F2 is equal to or exceeds the first force F1, the buoyant force on the buoyant member 140 causes the buoyant member 140 to move to close or increase a closing pressure upon the inlet port 120, as illustrated in FIG. 1. By contrast, when the first force F1 exceeds the opposing second force F2, the buoyant member 140 is moved to open the inlet port 120, at which point the bodily fluid will flow until the first force F1 is again matched by the second force F2. As illustrated in FIG. 1, the buoyant member 140 may be substantially spherical. Although not illustrated in FIG. 1, the inlet port 120 may be configured to readily accept the curved surface of the buoyant member 140 in order to form an improved seal to prevent leakage of the bodily fluid through the inlet port 120. In various example embodiments of the present general inventive concept, the buoyant member 140 may remain substantially seated in and centrally aligned with the inlet port regardless of valve orientation.

The gravitational pressure regulating valve 100 may include a guide member in the fluid chamber 110 to facilitate movement of the buoyant member 140 in a bidirectional manner. In other words, the guide member may cause the buoyant member 140 to move only directly to and away from the inlet port 120, to prevent the buoyant member 140 from moving to a position that inhibits the closing of the inlet port 120. In the example embodiment illustrated in FIG. 1, a permeable guide member 150 is provided in the form of a cage that guides the buoyant member 120 to and away from the inlet port 120. The permeable guide member 150 may be cylindrical, and configured to have a diameter only slightly larger than that of the buoyant member 140, to further limit any movement not associated with the reciprocating opening and closing of the valve. The diameter of the permeable guide member 150 may be sufficiently smaller than that of the fluid chamber 110 such that a desired amount of fluid may surround the buoyant member 140 inside the fluid chamber 110. The opposing force, F2, created by the buoyancy member 140, results in an opposition proportional to the gravitational angle of the buoyancy member 140, relative to the permeable guide member 150 and inlet port 120, whereby the force vector F2 becomes a component of the overall buoyancy force which is in alignment with the gravitational field. Therefore, the opposing force, F2, gradually reduces as the patient reclines to a minimum in the horizontal position, relative to the gravitational field and then gradually to a maximum when in a standing position.

Figure 2:
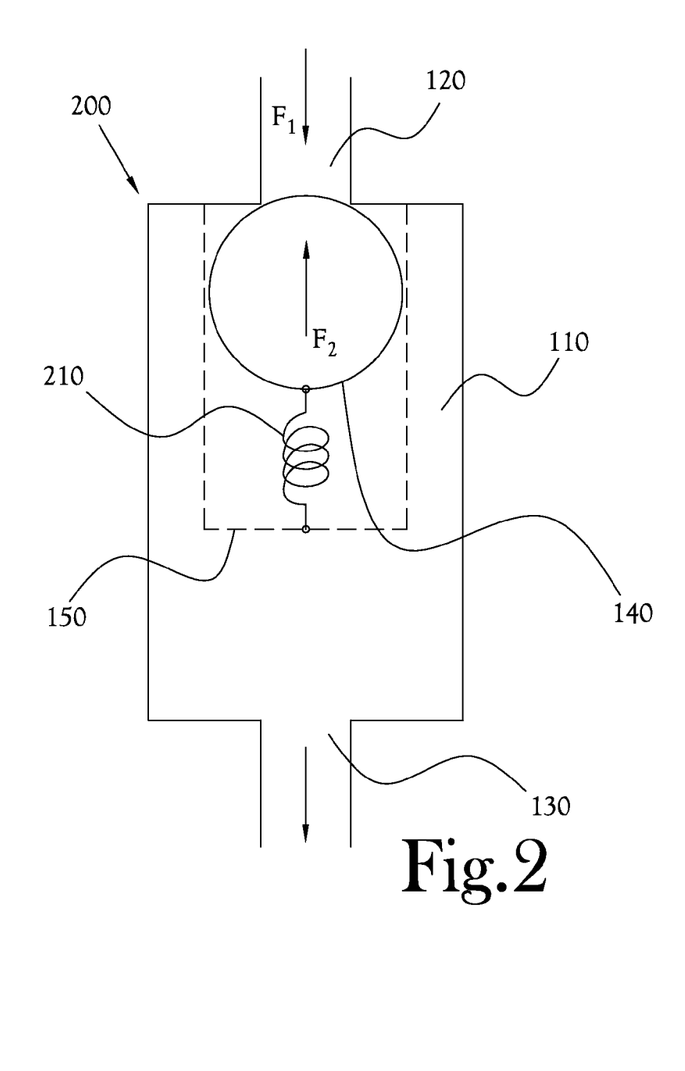
FIG. 2 illustrates the valve of FIG. 1 with an auxiliary bias member according to an example embodiment of the present general inventive concept.

In a situation in which the patient and valve are horizontal, the gravitational component of the second force F2 approaches zero. Therefore, to adjust the opposing second force F2 such that a desired second force F2 exists in the supine position, additional elements may be added to augment the second force F2. FIG. 2 illustrates the valve of FIG. 1 with an auxiliary bias member according to an example embodiment of the present general inventive concept. The auxiliary bias member is in the form of a spring 210 which couples the buoyant member 140 to the permeable guide member 150 and biases the buoyant member 140 in the direction of the inlet port 120. Thus, when the patient and valve are in the horizontal position, the force provided by the spring 210 may be the only component of the second force F2. In situations in which the patient is more upright than the horizontal position, the buoyant force resulting from the increased gravitational pressure is combined with the force of the spring to result in the total second force F2. With the additional opposing force provided by the biasing member, the bodily fluid does not freely flow into the fluid chamber 110 in the event that no buoyant force is present on the buoyant member 140. As a result, the bodily fluid may flow at the desired rate by only overcoming the biasing force of the spring 210 when the patient is supine, but additional gravitational force on the bodily fluid is countered by a proportional counterforce due to the buoyant force on the buoyant member 140 when the patient is more upright.

While only one buoyant member 140 is illustrated in FIGS. 1-2, it is understood that two or more buoyant members may be provided inside the fluid chamber 150 to provide additional buoyant force to the opposing second force F2. In an embodiment in which the permeable guide member is provided, the two or more buoyant members may be provided in line inside the guide member.

Figure 3:
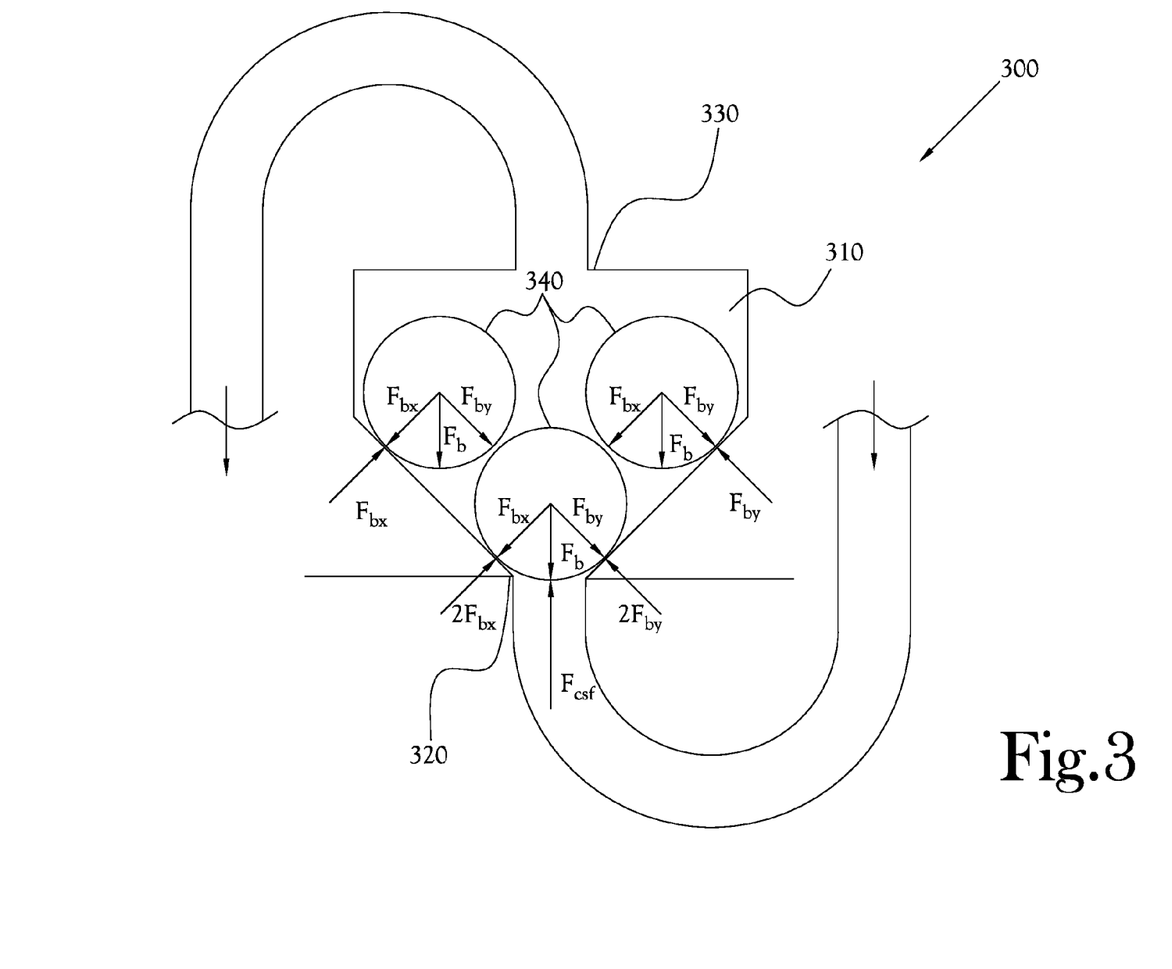
FIG. 3 illustrates a gravitational pressure regulating valve according to another example embodiment of the present general inventive concept.
Figure 4A:
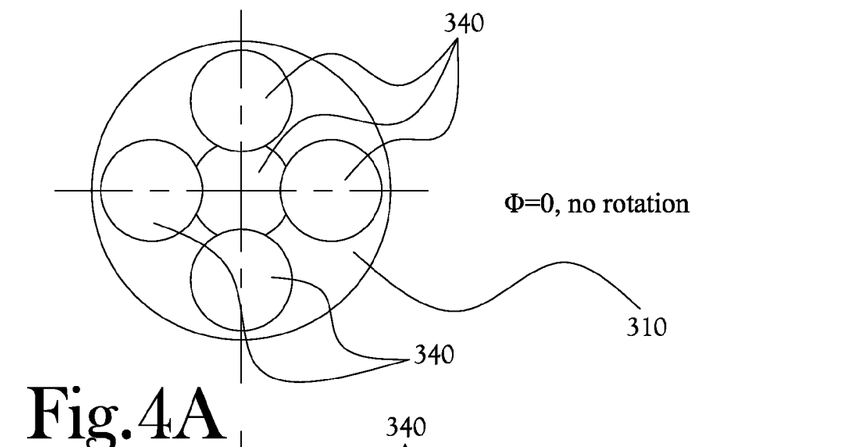
FIGS. 4A-C illustrate a top view of the opposing force members illustrated in FIG. 3 at varying degrees of rotation of the gravitational pressure regulating valve.
Figure 4B:
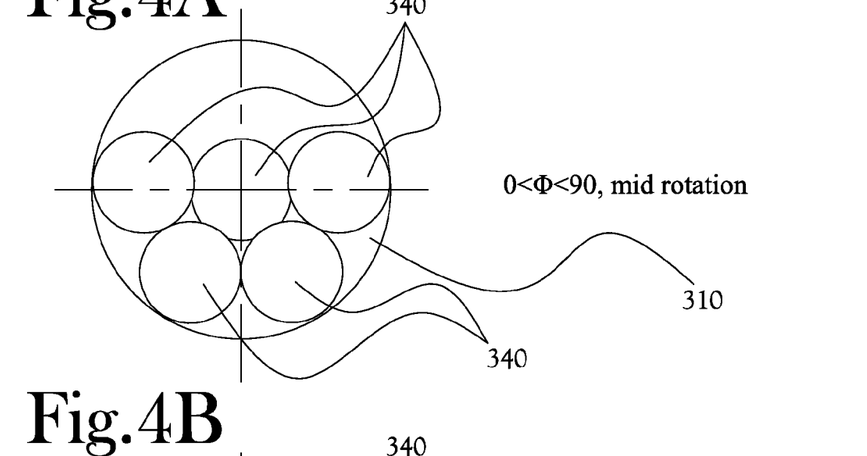
Figure 4C:
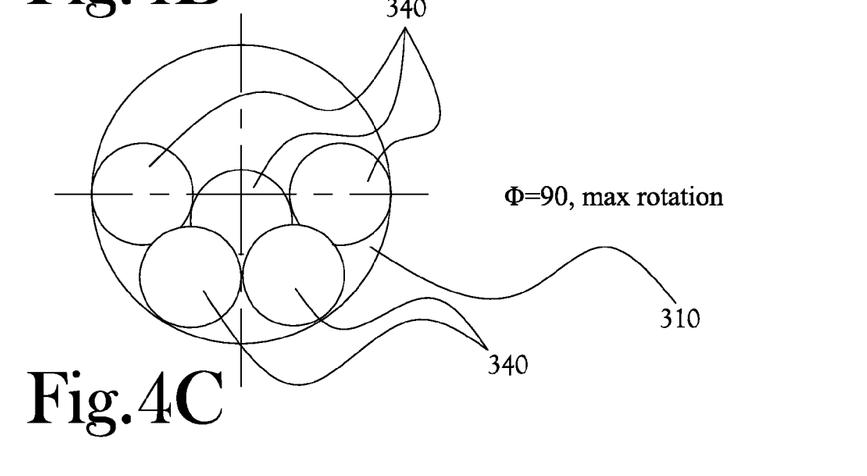

FIG. 3 illustrates a gravitational pressure regulating valve according to yet another example embodiment of the present general inventive concept, and FIGS. 4A-C illustrate a top view of the opposing force members illustrated in FIG. 3 at varying degrees of rotation of the gravitational pressure regulating valve. The example embodiments of FIGS. 1-2 are configured such that the bodily fluid enters an inlet port at or near the top of the valve when oriented in a vertical position, and therefore employ buoyant members to provide a counter force to the fluid flow. By contrast, the example embodiment of FIGS. 3-4C is configured such that the bodily fluid enters an inlet port at or near the bottom of the valve when oriented in a vertical position, and therefore employs weighted members having a greater density than the bodily fluid, so that the weight of the weighted members provides the counter force. Thus, while the embodiments illustrated in FIGS. 1-4C are all illustrated in the most vertically oriented positions, the bodily fluid flows down through the inlet port into the fluid chamber in FIGS. 1-2, while the bodily fluid flows up through the inlet port into the fluid chamber in FIGS. 3-4C. However, it is understood that, as indicated in the drawings, the origin of the bodily fluid is "above" the valves in all of the drawings, and is simply routed by the tubing to enter the valves from the underside in the example embodiment illustrated in FIGS. 3-4C.

The example embodiment of the gravitational pressure regulating valve 300 illustrated in FIG. 3 includes a fluid chamber 310 with an inlet port 320 to receive a bodily fluid and an outlet port 330 to discharge the received bodily fluid, and a plurality of weighted members 340 in the fluid chamber to oppose a first force F1 of the fluid flow at the inlet port 320 with an opposing second force F2 that varies according to changes in the gravitational pressure on the weighted members 340 due to the orientation of the valve. In FIG. 3, the first force F1 is represented as $F_{csf}$, the force of CAF siphoning, and the second force F2 is represented as $F_b$, which is generated by the weighed members 340. As illustrated in FIG. 3, at least a portion of an inner surface of the fluid chamber 310 is provided in a substantially conical shape around the inlet port 320 such that a first one of the weighted members 340 is guided by gravity to rest in and close the inlet port 320 when the second force F2 is greater than the first force F1. Also, the conical shape of the inner surface of the fluid chamber 310 causes the remaining weighted members 340 to be offset in a horizontal and vertical direction from the first weighted member 340. As illustrated in this embodiment, the weighted members may be substantially spherical.

As illustrated in FIG. 3, the gravitational forces of the weighted members in the direction of the second force F2 can be viewed as component force vectors in the x and y directions indicated in the drawing. Due to the first weighted member 340 being offset in the vertical and horizontal directions from the remainder of the weighted members 340, portions of the total gravitational forces from those weighted members 340 are added to the opposing force provided by the weight of the first weighted member 340. Thus, not only is the total opposing second force F2 increased by such an arrangement, but more stability is provided to the closing force when the valve is tilted away from the vertical orientation, until the valve is horizontal, at which point the gravitational force of the weighted members 340 is at a minimum value. The center of mass generated by the plurality of the weighted members 340 counters the force due to siphoning when the patient is upright from the horizontal position. That center of mass shifts with incline angle until the minimum opposing force is produced at the horizontal position, at which the desired fluid set point should control the opening of the inlet port 320. Various values of either the number or the size of the weighted members can be selected to compensate for patient height.

FIG. 4A is a top view of a partial cross section of the valve of FIG. 3. In this drawing, the valve is at a vertical orientation, and therefore the first weighted member 340 is closing the inlet port 320, and the remaining weighted members 340 are providing substantially equal weights to the first weighted member 340. At this vertical orientation, indicated as having "no rotation" in the drawing, the combined center of mass of the weighted members 340 opposes the first force F1 that is the effect of siphoning. Due to the configuration of the weighted members 340 and the conical inner surface of the fluid chamber 310, the opposing force is proportional to the rotation of the valve, as is the force F1 due to the bodily fluid siphoning. As illustrated in FIGS. 4B-C, the shifting center of mass of the weighted members 340 opposes, or counters, the first force F1 due to siphoning as the rotation angle increases. In FIG. 4C, at the maximum rotation, or horizontal position, the opposing second force F2 has reached the minimum magnitude.

It is noted that while five weighted members 340 have been illustrated in the example embodiment described above, various other example embodiments of the present general inventive concept may utilize more or less of the weighted members. Also, various example embodiments may provide a fluid chamber 310 that is formed to limit the movement of the weighted members such that the first one of the weighted members will always be in contact with at least one remaining weighted member.

Figure 5:
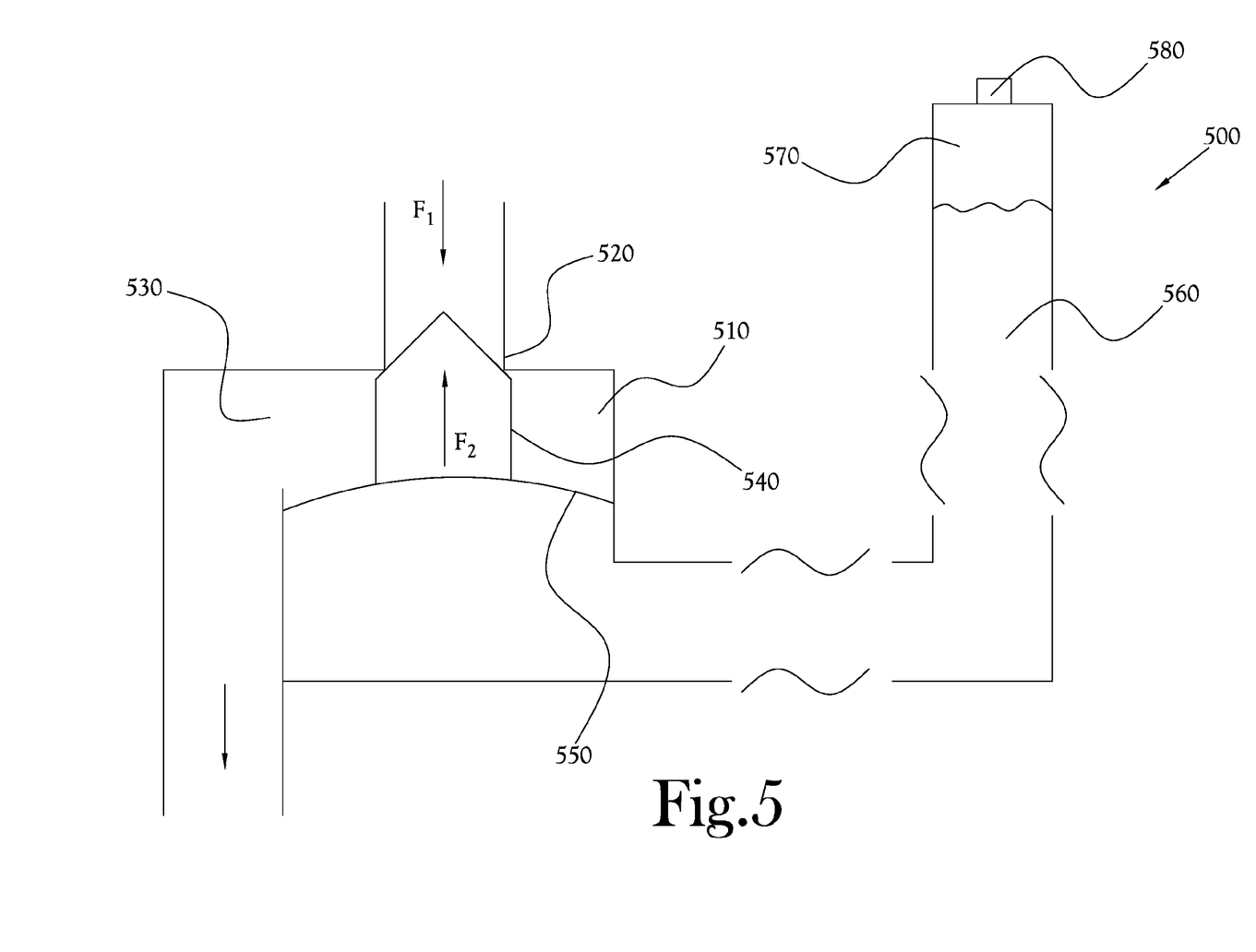
FIGS. 5-6 illustrate a gravitational pressure regulating valve according to yet another example embodiment of the present general inventive concept.
Figure 6:
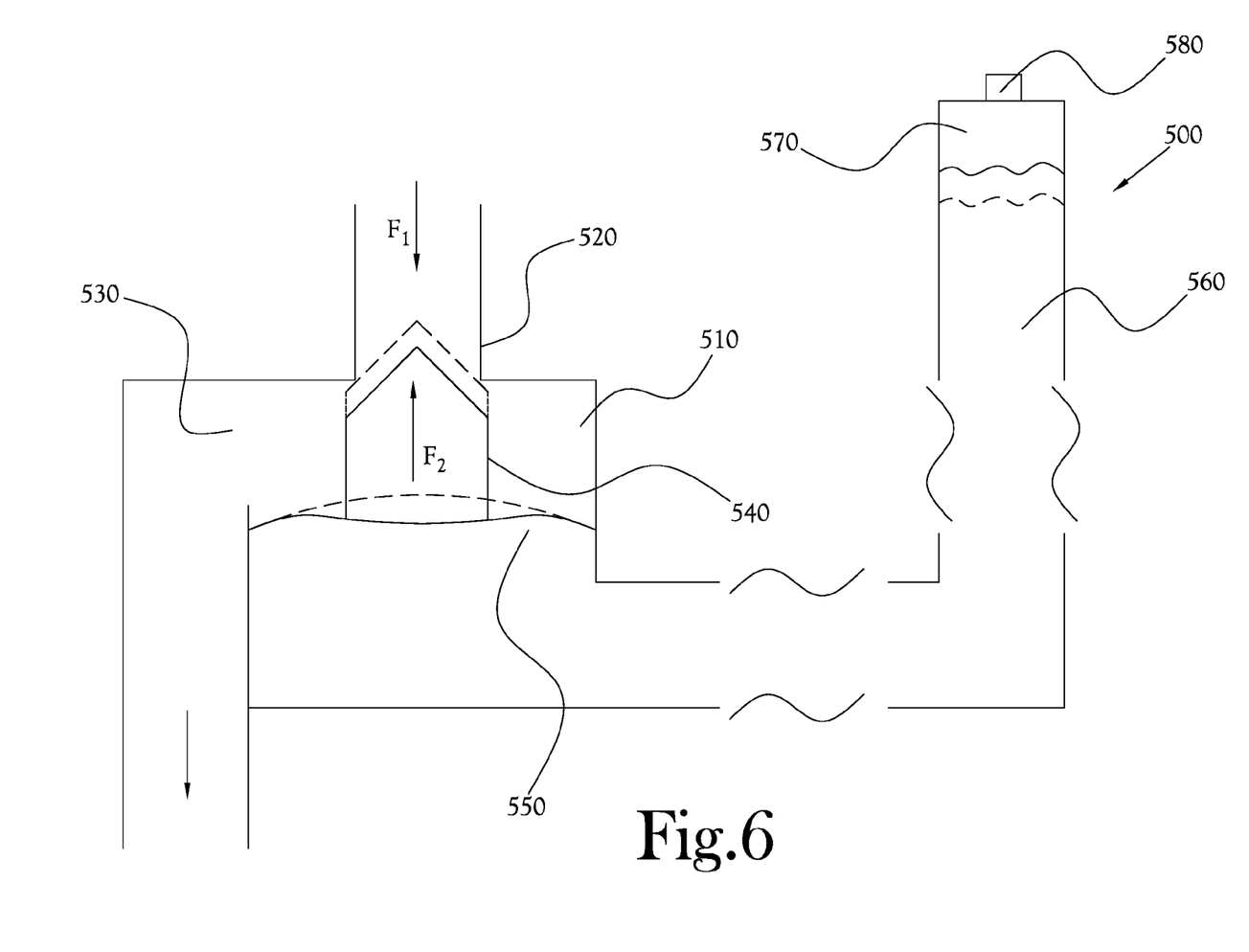

FIGS. 5-6 illustrate a gravitational pressure regulating valve according to yet another example embodiment of the present general inventive concept. The gravitational pressure regulating valve 500 in FIG. 5 includes a fluid chamber 510 with an inlet port 520 to receive a bodily fluid and an outlet port 530 to discharge the received bodily fluid, a variable resistance flow valve 540 provided in the fluid chamber to oppose a first force F1 of the fluid flow at the inlet port with a second force F2 applied to the variable resistance flow valve 540, an opposing force member 550 to apply the second force F2 to the variable resistance flow valve 540, and a reference unit 560 that is sensitive to gravitational pressure changes to cause the opposing force member 550 to vary the second force according to the gravitational pressure changes. In this example embodiment, the opposing force member is a diaphragm 550 coupled to the variable resistance flow valve 540, and the reference unit 560 is a reference fluid column 560 in direct communication with the diaphragm 550. The diaphragm 550 prevents fluid in the reference fluid column 560 from entering a portion of the fluid chamber 510 through which the bodily fluid flows. Changes in gravitational pressure applied to the reference fluid column 560 cause the diaphragm 550 to move upward or downward to increase or decrease the opposing second force F2. The device 500 may also include a predetermined amount of gas 570 forming an interface with the reference fluid column 560 to allow compression to the diaphragm resulting from the first force F1 being greater than the opposing second force F2. Various example embodiments of the present general inventive concept may also provide an air bleeder port 580 to a housing containing the reference fluid column 560 to be used to remove air from the housing when being filled with liquid.

FIG. 5 illustrates the device 500 at a vertical orientation at which the gravitational pressure is greatest on the reference fluid column 560, and therefore the opposing second force F2 is at a maximum value. As the device 500 is rotated according to the patient's position, the gravitational pressure on the reference fluid column 560 will be reduced, and the opposing second force F2 will be reduced in turn, reaching a minimum value when the device is at a horizontal position. In FIG. 5, the second force F2 is still equal to or exceeding the first force F1 of the bodily fluid at the inlet port 520. FIG. 6 illustrates the same device 500 after the first force F1 has overcome the opposing second force F2. As indicated in the drawing, the variable resistance flow valve 510 has been pushed down to open the inlet port 520, which in turn caused the diaphragm 550 to be pressed down, compressing the area of the reference fluid column 560 and decreasing the volume of the gas 570. The inlet port 520 will remain at least partially open until the opposing second force F2 again matches or exceeds the first force F1. In other words, once the excess pressure due to an excess of the bodily fluid needing to be drained is decreased, and the opposing second force F2 again counters the first force F1 caused by gravity and the weight of the draining fluid, the inlet port 520 will be closed.

It is noted that various components illustrated in FIGS. 1-7 may be omitted or substituted for, changed in shape or configuration, and so on. For example, the variable resistance flow valve 510 is illustrated as having a conical top accommodated by the inlet port 520, but any of several possible shapes and configurations may be used instead. Also, the reference unit of the device 500 is a directly connected reference fluid column that transfers gravitational pressure directly to a diaphragm. However, various other example embodiments may employ reference units that simply sense the gravitational pressure and control the opposing force member and/or variable resistance flow valve through other mechanical connections, or by electrical communication. For example, the reference unit may include a gravitational pressure sensor, and may be in electrical communication with the opposing force member to cause the opposing force member to vary the second force according to the gravitational pressure changes.

Figure 7:
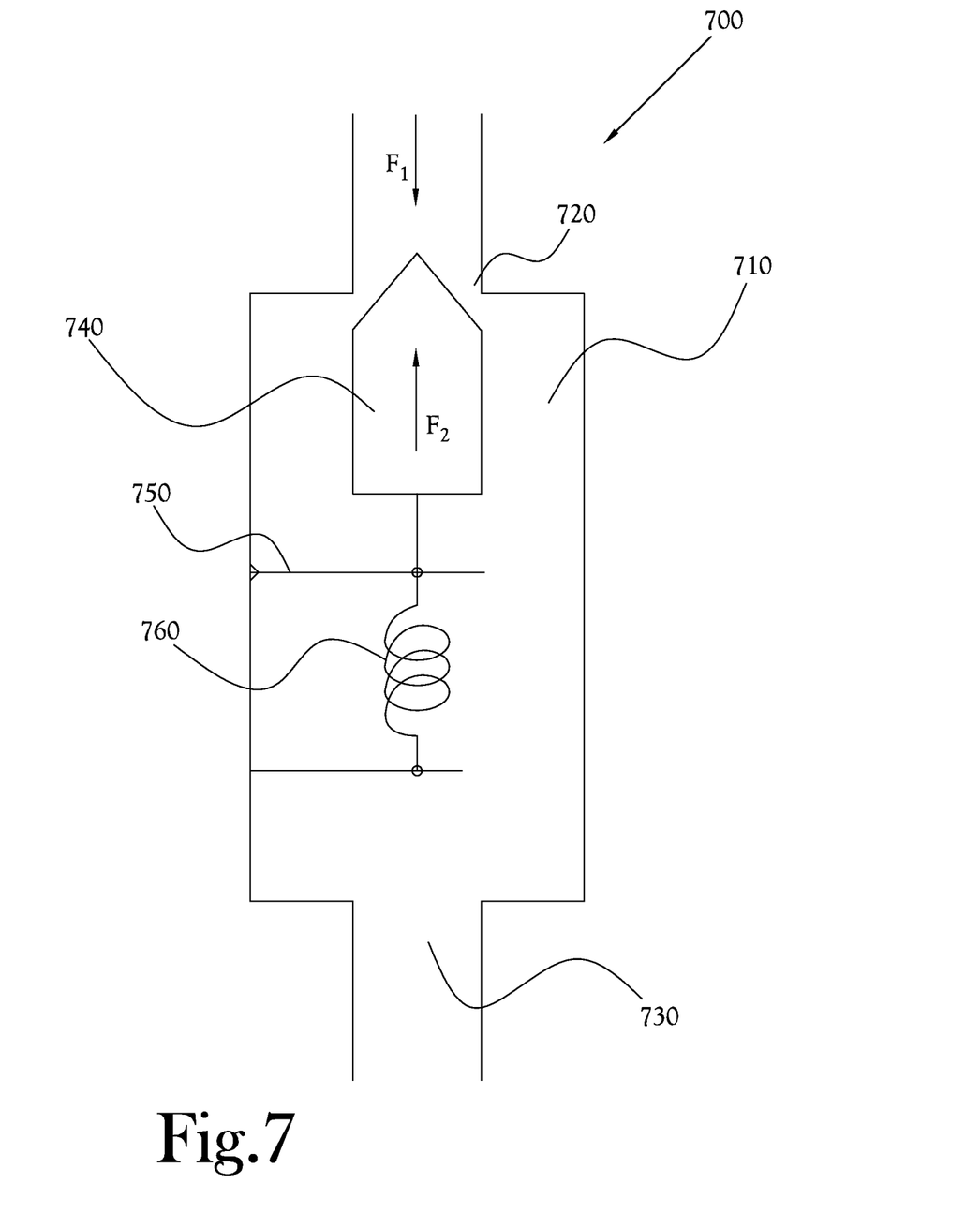
FIG. 7 is a schematic illustration of various elements of a gravitational pressure regulating valve according to still another example embodiment of the present general inventive concept.

FIG. 7 is a schematic illustration of various elements of a gravitational pressure regulating valve according to still another example embodiment of the present general inventive concept. The gravitational pressure regulating valve 700 of FIG. 7 includes a fluid chamber 710 having an inlet port 720 and an outlet port 730, and a buoyant member 740 provided in the fluid chamber 710. Fluid flows into the inlet port 720 at the first force F1, and the buoyant member 740 opposes the fluid flow with the opposing second force F2.

When the opposing second force F2 is equal to or exceeds the first force F1, the buoyant force on the buoyant member 740 causes the buoyant member 740 to move to close the inlet port 720. By contrast, when the first force F1 exceeds the opposing second force F2, the buoyant member 740 is moved to open the inlet port 720, at which point the bodily fluid will flow until the first force F1 is again matched by the second force F2. As illustrated in FIG. 7, the buoyant member 740 may have a substantially conical tip that is received by the inlet port 720. The gravitational pressure regulating valve 700 may include a guide member in the fluid chamber 710 to facilitate movement of the buoyant member 740 in a bidirectional manner. In the example illustrated in FIG. 7, the guide member is hinged member 750 that is coupled to the fluid chamber 710 and the buoyant member 740 such that the movement of the buoyant member 740 is restricted to substantially bidirectional movement toward and away from the inlet port 720. This coupling configuration may include a hinged connection at either end of the hinged member 750. Further, the gravitational pressure regulating valve 700 may include a biasing member to increase the opposing second force F2. In the example embodiment illustrated in FIG. 7, the biasing member is a spring 760 that is coupled to the fluid chamber 710 and the hinged member 750. The biasing force of the spring may be chosen to tune the opposing second force F2 to the desired strength at a horizontal orientation of the valve 700, at which point the buoyant force due to gravitational pressure is at a minimum value.

Various example embodiments of the present general inventive concept provide an antisiphon device that prevents siphoning in a hydrocephalus shunt system. The antisiphon device may have an inlet, an outlet, a fluid chamber, a variable resistance flow valve responsive to CSF force or pressure, an opposing force or pressure generation element for variable adjustment, responsive to a gravitational field, of the flow valve, and an optional pressure element with further optional discrete or continuous pressure adjustment of the variable resistance flow valve.

The antisiphon device may be connected between a differential pressure relief valve normally used to control the intracranial pressure by removal of excess CSF fluid, and a distal exit catheter used in a hydrocephalus shunt treatment. There is generally no restriction on the general placement of the components used in a hydrocephalus system such as a flow transfer path between the cranium and peritoneal cavity or generally placed for a lumboperitoneal shunt. Optionally, the valve functionality contained in a shunt system could be incorporated into the functionality of the variable resistance flow valve and optional pressure element. The antisiphon device may be optionally positioned with manual placement, or automatic adjustment, or remote adjustment, to vertically align the inlet and outlet to align the device to be in the vertical direction when the patient is in the standing position.

The antisiphon device may prevent siphoning by balancing the force due to the weight of the CSF fluid contained within the shunt system with an opposing force element. The opposing force is substantially equal to the force generated by the weight of the CSF fluid, regardless of patient angle and activity without substantially restricting CSF fluid flow with regard to frictional or other losses. The opposing pressure element may be realized with a fixed or adjustable buoyancy device, relative to the CSF fluid, contained within the CSF fluid such that the buoyant opposing force is substantially equal to the gravitational force or weight generated by the CSF fluid contained within the shunt system. Furthermore, the difference between the forces or pressure of the CSF fluid in the shunt system compared to the opposing buoyancy force may be used to reduce or increase the resistance of the variable resistance flow valve and either restrict or enable CSF fluid flow between the antisiphon device's inlet and outlet. Furthermore, the antisiphon device's opposing force pressure generation element does not substantially restrict CSF fluid flow by substantially occupying the same volume contained within the substantial CSF fluid flow, and wherein the buoyancy device could be located in an adjacent or externally connected chamber and transmit valve control signals remotely. The antisiphoning device's opposing force or pressure element can substantially compensate for the effects of patient growth and maintain the ability to approximately oppose the additional force generated by the weight of the CSF fluid in the shunt system. The opposing pressure generation element can be adjustable and realized by adding or subtracting buoyancy elements to adjust the total opposing buoyancy force either during installation, later procedures, or through an internal mechanism which may be externally adjustable.

The opposing force or pressure generation element can also be a reference column of fluid aligned with the flow path with substantially equal length, or weight, containing an ideal gas forming an interface between the reference column of fluid and the column containment. The reference column could be attached to a fixed or adjustable fluid reservoir and/or a gas reservoir that is substantially large to allow free movement of the reference column. The interface between the reference fluid and ideal gas interface could be maintained by effects of surface tension or other forces which act to keep the liquid gas interface intact and prevents sloshing within the reference column. A flexible low resistance physical interface could be used to separate the liquid and gas as well. The movement of this interface is relative to the gravitational forces applied to the CSF fluid in the shunt system, including patient alignment, and the pressure differences between the reference column, and actual CSF fluid column with the shunt system. This movement can be used to adjust the resistance of the variable resistance pressure element by direct connection, mechanical or electrical control, or remote connection. The substantial effect is to compensate for the weight of the CSF fluid in the shunt system by negatively referencing it in the antisiphon device to the reference column of fluid. Thus, the flow of CSF in the shunt system substantially only depends on the CSF shunt system pressure differential across the pressure element. Additionally, the pressure element can further be configured to compensate for the additional flow generation or pressure generation due to the fluid velocity of the CSF fluid flowing in the shunt system. The pressure generated by the CSF flow velocity depends on column height and tubing size and can substantially contribute to parasitic drainage. Furthermore, the pressure element can be configured to compensate for other pressure error generators such as, but not limited to, tubing flow resistance differences, tubing size differences, tubing length differences, column height differences, etc. The operation of the variable resistance member and pressure element additionally can be combined into a single element to simultaneously compensate for CSF siphoning and set the CSF pressure drainage pressure threshold. The length of the tubes, in both the reference column and actual shunt CSF column, can automatically increase in length as the patient grows by implantation of extra tube length or other tube length increasing device. The relative relationship between the reference tube and actual CSF shunt tubing can be further scaled for more optimum control of the variable resistance pressure element. Furthermore, the reference column can be a complete column of fluid without an ideal gas interface with a fluid filled connection to a bladder or reservoir capable of transmitting surrounding environmental pressure into the reference fluid column. For example a completely fluid filled reference column connection to a bladder that is placed in the atmosphere or peritoneal cavity will transfer the surrounding environmental pressure into the reference column of fluid.

Diagnostic tools can be optionally incorporated into the antisiphoning structure to aid the care giver in determining shunt system functionality. Such as operation verification through a needle access port with an operationally responsive device integrated into the antisiphon structure. Active or passive diagnostic structures could be used to manually or automatically determine operation by measuring events triggered by CSF flow. For example determining positional movement of the variable resistance member and pressure element is an indication of CSF flow and further the movement rate is an indication of CSF flow rate. Additionally, the antisiphon device can be incorporated in an External Drainage System (EDS) or other monitoring systems to aid in the treatment of elevated intracranial CSF pressure.

According to various embodiments of the present general inventive concept, a gravitational pressure regulating valve to regulate fluid flow in a patient, including a fluid chamber having an inlet port to receive a bodily fluid and an outlet port to discharge the received bodily fluid, and an opposing force member in the fluid chamber to oppose a first force of the fluid flow at the inlet port with a second force that varies according to changes in gravitational alignment, is provided. Various example embodiments of the present general inventive concept may use buoyant or weighted members as the opposing force members. Other various example embodiments my use gravitational pressure sensors in mechanical or electrical communication with opposing force members to control the amount of opposing force applied to the fluid flow. Also, various example embodiments described herein as employing buoyant members may be used with weighted members by simply reversing the orientation of the fluid chambers and inlet/outlet ports, just as various example embodiments described as employing weighted members may be used with buoyant members by reversing the orientation of the fluid chambers and inlet/outlet ports.

Various example embodiments of the present general inventive concept may be used according to various attributes of the patient to be treated. For example, it may be more desirable to use a weighted member configuration for short tubing compensation in a shorter patient, and a buoyancy device for long tube compensation in a taller patient. Also, interchangeability of different embodiments allows for combining embodiments to more efficiently offer a more customizable patient-centered anti-siphoning solution so that a customizable multi-embodiment solution is used on a patient. Different configurations may be made available in assembly kits such that different embodiments of the present general inventive concept may be combined according to the unique needs of each patient. For example, various assembly kits may include modular components such that more than one buoyant member and/or weighted member configuration can be combined, a buoyant member configuration may be combined with a weighted member configuration, and so on. As another example, various assembly kits may provide additional buoyant and/or weighted members for customizing the counter force F2 according to the unique needs of the patient.

It is noted that the simplified diagrams and drawings do not illustrate all the various connections and assemblies of the various components, however, those skilled in the art will understand how to implement such connections and assemblies, based on the illustrated components, figures, and descriptions provided herein, using sound engineering judgment.

Numerous variations, modifications, and additional embodiments are possible, and accordingly, all such variations, modifications, and embodiments are to be regarded as being within the spirit and scope of the present general inventive concept. For example, regardless of the content of any portion of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated.

While the present general inventive concept has been illustrated by description of several example embodiments, it is not the intention of the applicant to restrict or in any way limit the scope of the inventive concept to such descriptions and illustrations. Instead, the descriptions, drawings, and claims herein are to be regarded as illustrative in nature, and not as restrictive, and additional embodiments will readily appear to those skilled in the art upon reading the above description and drawings.

The invention claimed is:

1. A gravitational pressure regulating valve to regulate fluid flow of a patient, comprising:
    a fluid chamber having an inlet port to receive a bodily fluid and an outlet port to discharge the received bodily fluid;
    a variable resistance flow valve provided in the fluid chamber and configured to oppose a first force of the fluid flow at the inlet port with a second force applied to the variable resistance flow valve;
    an opposing force member configured to apply the second force to the variable resistance flow valve; and
    a reference unit sensitive to gravitational alignment changes to cause the opposing force member to vary the second force according to the gravitational alignment changes,
    wherein the reference unit includes a reference fluid column in direct communication with the opposing force member; and
    the reference fluid column is configured such that changes in gravitational alignment of the reference fluid column correspond to changes in gravitational pressure of bodily fluid at the inlet port.

2. The gravitational pressure regulating valve of claim 1, wherein the opposing force member is a diaphragm coupled to the variable resistance flow valve.

3. The gravitational pressure regulating valve of claim 2, wherein the diaphragm separates the bodily fluid and fluid from the reference fluid column.

4. The gravitational pressure regulating valve of claim 3, further comprising a predetermined amount of gas forming an interface with the reference fluid column to allow compression in the diaphragm resulting from an opening of the variable resistance flow valve.

5. The gravitational pressure regulating valve of claim 4, further comprising a housing to house the reference fluid column and gas; and
    an air bleeder port to remove air from the housing when the housing is being filled with liquid.

6. The gravitational pressure regulating valve of claim 1, wherein the reference unit includes a gravitational alignment sensor, and is in electrical communication with the opposing force member to cause the opposing force member to vary the second force according to the gravitational alignment changes.

7. A gravitational pressure regulating valve to regulate fluid flow of a patient, comprising:
    a fluid chamber having an inlet port to receive a bodily fluid and an outlet port to discharge the received bodily fluid;
    a variable resistance flow valve provided in the fluid chamber and configured to oppose a first force of the fluid flow at the inlet port with a second force applied to the variable resistance flow valve;
    an opposing force member configured to apply the second force to the variable resistance flow valve; and
    a reference unit sensitive to gravitational alignment changes to cause the opposing force member to vary the second force according to the gravitational alignment changes,
    wherein the opposing force member is a diaphragm coupled to the variable resistance flow valve, the reference unit includes a reference fluid column in direct communication with the diaphragm, the diaphragm separates the bodily fluid and fluid from the reference fluid column, and the reference fluid column is configured such that changes in gravitational alignment of the reference fluid column correspond to changes in gravitational pressure of bodily fluid at the inlet port.

8. The gravitational pressure regulating valve of claim 7, wherein the reference fluid column includes a housing to house the reference fluid column and a predetermined amount of gas to form an interface between the fluid within the reference fluid column and the housing.

9. The gravitational pressure regulating valve of claim 8, wherein the reference fluid column includes a bleeder port to remove air from the reference fluid column.

\* \* \* \* \*